United States Patent
Sato et al.

(10) Patent No.: US 8,283,625 B2
(45) Date of Patent: Oct. 9, 2012

(54) METHOD OF PREPARING SAMPLE FOR MATRIX-ASSISTED LASER DESORPTION IONIZATION MASS SPECTROMETRY AND MATRIX-ASSISTED LASER DESORPTION IONIZATION MASS SPECTROMETRY

(75) Inventors: Taka-aki Sato, Kyoto (JP); Yutaka Aoki, Kyoto (JP); Takashi Shimada, Kyoto (JP); Atsuhiko Toyama, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 75 days.

(21) Appl. No.: 12/443,461

(22) PCT Filed: Sep. 21, 2007

(86) PCT No.: PCT/JP2007/069134
§ 371 (c)(1),
(2), (4) Date: Mar. 27, 2009

(87) PCT Pub. No.: WO2008/038812
PCT Pub. Date: Apr. 3, 2008

(65) Prior Publication Data
US 2010/0038529 A1 Feb. 18, 2010

(30) Foreign Application Priority Data
Sep. 28, 2006 (JP) .................................. 2006-265349

(51) Int. Cl.
*B01D 59/44* (2006.01)
(52) U.S. Cl. ........................................ 250/282; 250/281
(58) Field of Classification Search .................. None
See application file for complete search history.

(56) References Cited

U.S. PATENT DOCUMENTS

| | | | | |
|---|---|---|---|---|
| 6,024,925 A | * | 2/2000 | Little et al. | 422/507 |
| 6,268,131 B1 | * | 7/2001 | Kang et al. | 435/5 |
| 6,633,031 B1 | * | 10/2003 | Schultz et al. | 250/288 |
| 6,768,107 B2 | * | 7/2004 | Schultz et al. | 250/288 |
| 6,787,766 B2 | * | 9/2004 | Schultz et al. | 250/288 |

(Continued)

FOREIGN PATENT DOCUMENTS

EP 1 550 862 A1 7/2005

(Continued)

OTHER PUBLICATIONS

Meier et al., "Automated multiple-layer spotting for matrix-assisted laser desorption/ionization time-of-flight mass spectrometry of synthetic polymers utilizing ink-jet printing technology", ink-jet printing technology Rapid Communications in Mass Spectrometry, vol. 17, No. 20, Oct. 17, 2003, pp. 2349-2353.* Notification of Reasons for Refusal for the Application No. 2008-536466 from Japan Patent Office mailed May 24, 2011.

(Continued)

*Primary Examiner* — David A Vanore
*Assistant Examiner* — Andrew Smyth
(74) *Attorney, Agent, or Firm* — Cheng Law Group, PLLC

(57) ABSTRACT

It is intended to provide a method of preparing sample for matrix-assisted laser desorption/ionization mass spectrometry using a matrix capable of generating preferred crystals that cause effective ionization of a molecule to be measured. A method of preparing a sample for matrix-assisted laser desorption/ionization mass spectrometry comprising the steps of: preparing a solution of 2,5-dihydroxybenzoic acid of 40 mg/mL to saturated concentration as a matrix solution; and dispensing the matrix solution to a sample to be analyzed by using an inkjet mechanism, to crystallize the 2,5-dihydroxybenzoic acid.

8 Claims, 9 Drawing Sheets

U.S. PATENT DOCUMENTS

| | | | |
|---|---|---|---|
| 6,818,394 | B1* | 11/2004 | O'Donnell-Maloney et al. ............... 435/6.11 |
| 6,822,231 | B2* | 11/2004 | Schultz et al. ............... 250/288 |
| 7,095,018 | B2* | 8/2006 | Barnes et al. ............... 250/288 |
| 7,169,616 | B2* | 1/2007 | Johnson et al. ............... 436/180 |
| 7,285,422 | B1* | 10/2007 | Little et al. ............... 436/180 |
| 7,294,468 | B2* | 11/2007 | Bell et al. ............... 435/6.14 |
| 7,381,373 | B2* | 6/2008 | Blake et al. ............... 250/284 |
| 2003/0170903 | A1* | 9/2003 | Johnson et al. ............... 436/100 |
| 2003/0189167 | A1* | 10/2003 | Schultz et al. ............... 250/281 |
| 2004/0016878 | A1* | 1/2004 | Schultz et al. ............... 250/281 |
| 2004/0041093 | A1* | 3/2004 | Schultz et al. ............... 250/288 |
| 2004/0058448 | A1* | 3/2004 | Apicella et al. ............... 435/471 |
| 2004/0202670 | A1* | 10/2004 | Apicella ............... 424/184.1 |
| 2004/0219588 | A1 | 11/2004 | Furuta |
| 2005/0006502 | A1* | 1/2005 | Schultz et al. ............... 239/690 |
| 2005/0019223 | A1* | 1/2005 | Platt et al. ............... 422/100 |
| 2006/0047106 | A1* | 3/2006 | Pavliak et al. ............... 530/350 |
| 2006/0051741 | A1* | 3/2006 | Tanaka et al. ............... 435/5 |
| 2006/0099691 | A1* | 5/2006 | Apicella et al. ............... 435/85 |
| 2006/0138319 | A1* | 6/2006 | Barnes et al. ............... 250/288 |
| 2006/0144331 | A1 | 7/2006 | Hanafusa et al. |
| 2006/0147959 | A1* | 7/2006 | Bell et al. ............... 435/6 |
| 2009/0162836 | A1* | 6/2009 | Widschwendter ............... 435/6 |

FOREIGN PATENT DOCUMENTS

| | | |
|---|---|---|
| JP | 2002-236108 A | 8/2002 |
| JP | 2003-098154 A | 4/2003 |
| JP | 2004-520001 A | 7/2004 |
| JP | 2004-347594 A | 12/2004 |
| JP | 2005-283123 A | 10/2005 |
| WO | WO-00/70060 A1 | 11/2000 |
| WO | WO-2004/031759 A1 | 4/2004 |
| WO | WO-2008/038813 A1 | 4/2008 |

OTHER PUBLICATIONS

Supplementary European Search Report for the Application No. EP 07 82 8875 dated Sep. 5, 2011.

Shimma, Shuichi et al., "A Novel Approach to in situ Proteome Analysis Using Chemical Inkjet Printing Technology and MALDI-QIT-TOF Tandem Mass Spectrometer", J. Mass Spectrom. Soc. Jpn., 2006, vol. 54, No. 4, pp. 133-139.

Li, Lingjun et al., "Peptide Profiling of Cells with Multiple Gene Products: Combining Immunochemistry and MALDI Mass Spectrometry with On-Plate Microextraction", Analytical Chemistry, 2000, vol. 72, No. 16, pp. 3867-3874.

Nakanishi, Tsuyoshi et al., "Direct MS/MS Analysis of Proteins Blotted on Membranes by a Matrix-Assisted Laser Desorption/Ionization-Quadrupole Ion Trap-Time-of-Flight Tandem Mass Spectrometer", Journal of Proteome Research, 2005, vol. 4, No. 3, pp. 743-747.

Aoki, Yutaka at al., "A Novel Method for Analyzing Formalin-Fixed Paraffin Embedded (FFPE) Tissue Sections by Mass Spectrometry Imaging", Proc. Jpn. Acad., 2007, vol. 83, No. 7, pp. 205-214.

International Preliminary Report on Patentability for the Application No. PCT/JP2007/069134 mailed Apr. 9, 2009.

International Search Report for the Application No. PCT/JP2007/069134 mailed Dec. 18, 2007.

Meier, Michael A. R. et al., "Automated multiple-layer spotting for matrix-assisted laser desorption/ionization time-of-flight mass spectrometry of synthetic polymers utilizing ink-jet printing technology", Rapid Communications in Mass Spectrometry, 2003, vol. 17, pp. 2349-2353.

Lemaire, Remi et al., "Direct Analysis and MALDI Imaging on Formalin-Fixed Paraffin-Embedded (FFPE) Tissues: Application to Parkinson Disease", Proceedings of the 54th ASMS Conference on Mass Spectrometry and Allied Topics, 2006, ThP333, p. 147.

* cited by examiner

Fig. 1
50mg/ml DHB 50%ACN 0.1%TFA
(a) Conventional Method
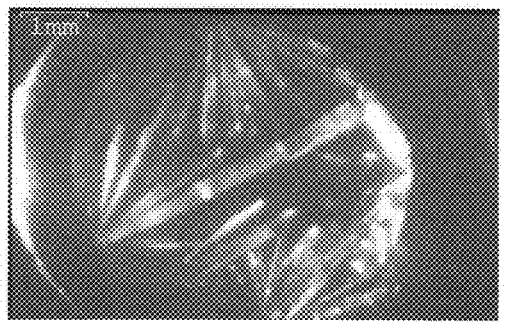
(b) Inkjet Method
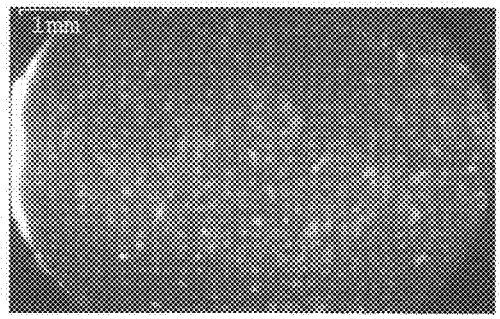

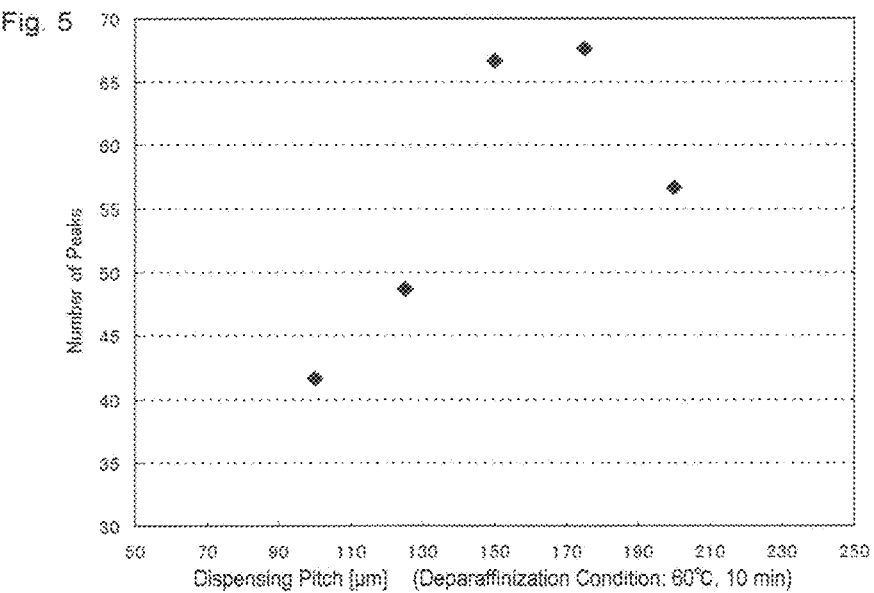
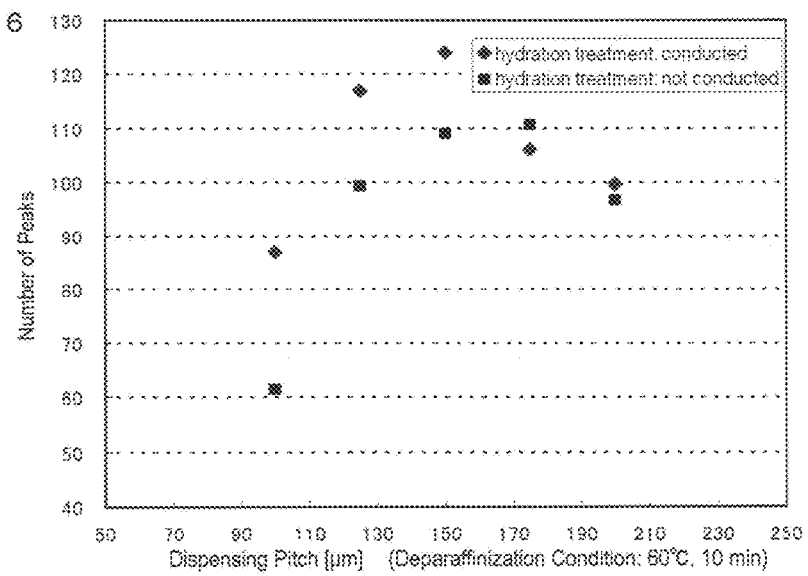

METHOD OF PREPARING SAMPLE FOR MATRIX-ASSISTED LASER DESORPTION IONIZATION MASS SPECTROMETRY AND MATRIX-ASSISTED LASER DESORPTION IONIZATION MASS SPECTROMETRY

TECHNICAL FIELD

The present invention pertains to a field of matrix-assisted laser desorption/ionization (MALDI) mass spectrometry. The present invention also pertains to medical and biological fields such as cell biology, pathology and biochemistry.

The present invention relates to a method of preparing sample for matrix-assisted laser desorption/ionization mass spectrometry and matrix-assisted laser desorption/ionization mass spectrometry. Concretely, the present invention relates to a MALDI mass spectrometry for a section specimen of a biological sample, and more particularly to a mass spectrometric imaging method for a section specimen of a biological sample.

BACKGROUND ART

<Matrix-Assisted Laser Desorption/Ionization (MALDI) Mass Spectrometry>

Recently, a soft ionization technique of a biological polymer was established by development of a method of matrix-assisted laser desorption/ionization (MALDI), and a research of proteomics has been rapidly advanced. In the MALDI mass spectrometry, to produce how uniform crystal by using a matrix is one of important factors involved in likelihood of ionization of the molecule to be measured, which greatly contributes to sensitivity, quantitative performance, reproducibility of the analysis. This is particularly important in an automatic analysis.

As for the kind of matrix, those considered to be effective tend to be limited according to the kind of molecule to be measured, the kind of mass spectrometer and the like. For example, in analysis of protein, sinapinic acid, $\alpha$-cyano-hydroxycinnamic acid and the like are considered as being effective as the matrix. On the other hand, these matrixes are considered as effective, for example, in an analysis of AXIMA-CFRplus (made by SHIMADZU CORPORATION).

On the other hand, an apparatus capable of dispensing a minute amount of a reagent solution is known. Such an apparatus is used usefully for preparing a sample for MALDI mass spectrometry. As an example of such an apparatus, apparatuses disclosed in Japanese Patent Application Laid-Open Publication No. 2003-98154 and Japanese Patent Application Laid-Open Publication No. 2005-283123 may be recited.
<Bioimaging>

In recent years, bioimaging techniques that directly observe cells and biological tissues for visually examining biological phenomena occurring in a living body have been developed and advanced. The bioimaging technique makes it possible to detect a biological molecule while keeping the positional information in the living body. In the bioimaging technique, a thin section of a biological tissue specimen (for example, a frozen section or a paraffin-embedded section) is used as a sample.

Regarding the paraffin-embedded section, today a great number of paraffin-embedded biological tissues used in pathological diagnoses and the like are preserved. The ability of acquiring information of biological molecules from these will allow investigation of diagnosis, therapy, pathologic finding, prognosis and the like in a retrospective manner using past cases, and hence is recognized as being a great advantage in a research of pathology of outbreak of disease, development of a new drug and so on.

As a means in the bioimaging, microscopy is used in most cases, and as other means, mass spectrometry may be used (namely, mass spectrometric imaging).

As an example of mass spectrometric imaging, for example, after subjecting a protein molecule contained in a tissue section to a treatment such as digestion as needed, mass spectrometry is conducted for a plurality of positions on a surface of the tissue section, and an image is formed from mass spectra obtained for respective positions on a surface of the tissue section.

In the mass spectrometric imaging, a frozen section of biological tissue is typically used as a sample. In recent years, for example, Japanese Patent Application Laid-Open Publication No. 2004-347594 reports subjecting a frozen biological tissue section to the MALDI mass spectrometry, and obtaining a MS spectrum. In this art, the matrix solution is microdispensed using inkjet mechanism.

Very recently, there is also reported to execute mass spectrometric imaging by using a paraffin section of a biological tissue. Concretely, 54th ASMS Conference on Mass Spectrometry collected programs, p 147 (Abstract of Session: Imaging MS II Code: ThP18 Time Slot/Poster Number: 333) reports that a paraffin section is subjected to a treatment by a usual immunocytochemical technique, and MALDI mass spectrometric imaging is conducted directly by using reactive matrix.

Patent Document 1: Japanese Patent Application Laid-Open Publication No. 2003-98154
Patent Document 2: Japanese Patent Application Laid-Open Publication No. 2005-283123
Patent Document 3: Japanese Patent Application Laid-Open Publication No. 2004-347594
Non-Patent Document 1: 54th ASMS Conference on Mass Spectrometry collected programs, p 147

DISCLOSURE OF THE INVENTION

Object of the Invention

In a protein analysis using a mass spectrometer such as AXIMA-CFRplus (made by SHIMADZU CORPORATION), even if sinapinic acid, $\alpha$-cyano-hydroxycinnamic acid or the like is considered as effective as a matrix, this mass spectrometry is unable to identify protein because this is unable to conduct two or more order of multi-stage MS.

In the above Japanese Patent Application Laid-Open Publication No. 2004-347594, microdispensing is conducted using an inkjet mechanism, crystals are likely to generate nonuniformly in the case of 2,5-dihydroxybenzoic acid. Therefore, it is necessary to apply a laser while visually checking the part where crystals generate nearly uniformly. Further, in the case of $\alpha$-cyano-hydroxycinnamic acid, an inkjet outlet is more likely to get clogged.

Quality of imaging according to the method described in abstract in p. 147 of the above collected programs for 54th ASMS Conference on Mass Spectrometry is expected to be low. One reason of the expectation is that preferable microdispensing of a matrix solution is not achieved, and crystals do not generate desirably.

Therefore, it is an object of the present invention to provide a method of preparing sample for matrix-assisted laser desorption/ionization mass spectrometry using a matrix capable of generating preferred crystals that cause effective ionization of a molecule to be measured. It is also an object of the present invention to provide a matrix-assisted laser desorption/ionization mass spectrometry capable of conducting an analysis of high sensitivity by effectively causing ionization of a molecule to be measured and capable of identifying a molecule to be measured by conducting a second or more order of multi-stage MS.

SUMMARY OF THE INVENTION

The present invention includes the following aspects (1) to (6).

<Method of Preparing Sample for Matrix-Assisted Laser Desorption/Ionization Mass Spectrometry>

(1) A method of preparing a sample for matrix-assisted laser desorption/ionization mass spectrometry comprising the steps of:

preparing a solution of 2,5-dihydroxybenzoic acid of 40 mg/mL to saturated concentration as a matrix solution; and dispensing the matrix solution to a sample to be analyzed by using an inkjet mechanism, to crystallize the 2,5-dihydroxybenzoic acid.

(2) The method of preparing a sample for matrix-assisted laser desorption/ionization mass spectrometry according to (1), wherein the sample to be analyzed is a section specimen of a biological sample.

(3) The method of preparing a sample for matrix-assisted laser desorption/ionization mass spectrometry according to (1) or (2), wherein the sample to be analyzed is derived from a paraffin-embedded specimen.

In the above (3), the wording what "is derived from a paraffin-embedded specimen" means a biological sample obtained by subjecting a paraffin-embedded specimen to an appropriate treatment for adaptation to mass spectrometry (for example, deparaffinization).

According to the method of the above (3), liquid droplets of matrix are unlikely to extend so that it is possible to produce microcrystals with excellent workability. Further, when the sample obtained in the method of above (3) is subjected to mass spectrometry, by obtaining data from a pathological specimen that has been stored for a long time from the past, it is possible to profile an expressed protein, and to correlate an expression pattern of protein and disease in a retrospective manner.

(4) The method of preparing a sample for matrix-assisted laser desorption/ionization mass spectrometry according to any one of (1) to (3), wherein the sample to be analyzed is held on a surface of an electrically conductive support.

(5) The method of preparing a sample for matrix-assisted laser desorption/ionization mass spectrometry according to any one of (1) to (4), wherein the matrix solution is dispensed at a dispensing pitch of 100 to 200 μm.

According to the method of above (5), it becomes possible to conduct mass spectrometric imaging with high quality when the obtained sample is subjected to mass spectrometry. Further, since microcrystals of a matrix can be deposited uniformly on the biological sample, it is possible to ionize the biological molecule to be measured on the biological sample stably and effectively, and it becomes possible to know localization as well as precise positional information.

<Matrix-Assisted Laser Desorption/Ionization Mass Spectrometry>

(6) A matrix-assisted laser desorption/ionization mass spectrometry, comprising the steps of:

preparing a sample for matrix-assisted laser desorption/ionization mass spectrometry by the method according to any one of the above (1) to (5), and measuring the sample by a mass spectrometer.

(7) The matrix-assisted laser desorption/ionization mass spectrometry according to (6), wherein in the step of measuring by a mass spectrometer, second or higher order of multi-stage MS is conducted.

The method of (7) enables identification of the measured molecule.

<Sample for Matrix-Assisted Laser Desorption/Ionization Mass Spectrometry>

(8) A sample for matrix-assisted laser desorption/ionization mass spectrometry prepared by the method according to any one of the above (1) to (5).

According to the present invention, it is possible to provide a method of preparing a sample for matrix-assisted laser desorption/ionization mass spectrometry for generating preferred crystals that allow effective ionization of a molecule to be measured regardless of the nature of the used matrix. Also according to the present invention, it is possible provide the matrix-assisted laser desorption/ionization mass spectrometry capable of conducting an analysis of high sensitivity by causing effective ionization of a molecule to be measured, and capable of identifying a molecule to be measured by conducting a second or higher order of multi-stage MS.

BRIEF DESCRIPTION OF THE DRAWINGS

FIG. 1(a) is a photograph of a crystal generated when a matrix solution of high concentration (50 mg/mL) is added dropwise with a micro pipette; and FIG. 1(b) is a photograph of a crystal generated when a matrix solution with a high concentration (50 mg/mL) is added dropwise with an inkjet mechanism;

FIG. 5 is a graph showing a result of mass spectrometry from a paraffin section using a method for heating-deparaffinization (heating condition: 60° C.—10 min.) according to the present invention (Example 5), in the form of relation between a dispensing pitch of a matrix solution and the number of peaks in mass spectrum;

FIG. 6 is a graph showing a result of mass spectrometry from a paraffin section according to a method for analysis of the present invention (deparaffinization condition: 60° C.—10 min.) in which a hydration treatment is conducted (Example 5) and a result of mass spectrometry from a paraffin section according to a method for analysis of the present invention (deparaffinization condition: 60° C.—10 min.) in which a hydration treatment is not conducted (Example 6), in the form of relation between a dispensing pitch of matrix solution and the number of peaks in mass spectrum;

MODES FOR CARRYING OUT THE INVENTION

1. Sample to be Analyzed

Figure 2:
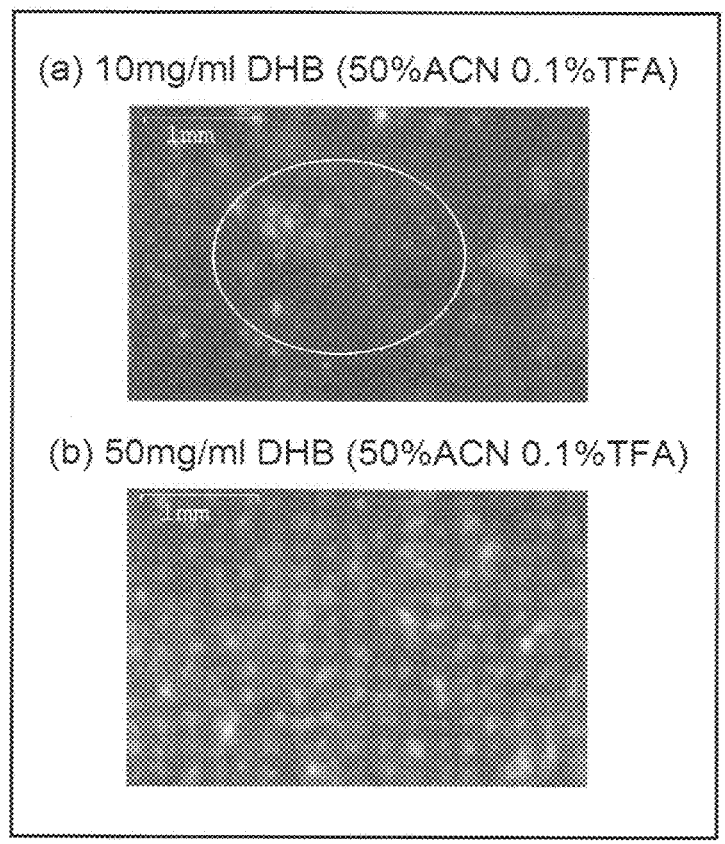
FIG. 2(a) is a photograph of a crystal generated from a matrix solution of low concentration (10 mg/mL)
FIG. 2(b) is a photograph of a crystal generated from a matrix solution of high concentration (50 mg/mL) (Example 1)

A sample to be analyzed in the present invention includes any samples that can be subjected to matrix-assisted laser desorption/ionization mass spectrometry (MALDI) using 2,5-dihydroxybenzoic acid (DHB) as a matrix.

[1-1. Biological Sample]

Typically, the sample to be analyzed is a biological sample containing a cell or a tissue of an organism. Such a biological sample may be derived from any organisms. As for animals, amphibian, reptile, bird, mammalian and the like are widely accepted, and particularly preferred is a specimen derived from mammalian. Among these, a specimen derived from mouse or human being is more preferred.

[1-2. Specimen]

Further, as the biological sample, those preserving an intact structure as it were in a living body such as a cell or a tissue may be used. A biological sample in such a condition is provided in most cases as a slice-formed specimen (section specimen) in which the biological sample is embedded in an appropriate embedding medium. As such a specimen, any specimens that can be targets of a research in any analyses including morphological, immunohistochemical, and enzymehistochemical analyses are intended. Therefore, the specimen may be any of full-body specimen, organ specimen, tissue specimen, embryo specimen and cell specimen of such a living body. Further, when the specimen is a pathologic specimen, the disease from which the living body suffers may be any of cancer, Alzheimer disease, Parkinson disease, ischemic cerebrovascular disease, and ischemic heart disease.

The above-described specimen may be a specimen for an analysis of pharmacokinetics. A specimen for analysis of pharmacokinetics is a specimen for verifying and evaluating the potentiality as a pharmaceutical agent from the viewpoint of dynamics in the body (absorption, distribution, metabolism and excretion), and concretely a specimen derived from a living body administered with a drug. In the analysis of such a specimen, presence of a pharmaceutical drug having reached a target site is examined, for example, by detecting a biological molecule to which the pharmaceutical agent binds.

Examples of the embedding medium of specimen include, but are not limited to, water, paraffin, celloidin, carbowax, gelatin, albumin, agarose, epoxy resin, polyester resin and the like, and water-soluble resin such as glycol methacrylate. In the present invention, as a section specimen, a frozen section using water as an embedding medium, and a paraffin section using paraffin as an embedding medium (hereinafter, also referred to as a paraffin-embedded specimen) are often used.

The frozen section may be subjected to the present invention by returning to room temperature, while the other section specimen may be made into an exposed section specimen by conducting an appropriate treatment for adaptation to mass spectrometry (for example, a treatment of removing an embedding medium). The term exposure means that from a specimen in which a biological sample is embedded in an embedding medium, the embedding medium elutes and the biological sample is exposed. A section specimen of a biological sample in such a condition may be subjected to the present invention.

In the present invention, the case of using a paraffin-embedded specimen is particularly preferred. Also in the case of a paraffin-embedded specimen, it may be brought into a section specimen in which the biological sample is exposed from the paraffin by conducting an appropriate treatment for adaptation to mass spectrometry (for example, a treatment of removing paraffin). A section specimen of a biological sample in such a condition may be subjected to the present invention.

A section specimen of a biological sample derived from paraffin-embedded specimen is advantageous in that microcrystals of a matrix are easily formed, workability is excellent and a preferable analytical result can be obtained. Furthermore, the bioimaging technique using a paraffin-embedded section as a sample is superior to the case using a frozen section as a sample, in that it is also effective in pathological diagnosis which allows retrospective study and has versatility.

As for a paraffin-embedded specimen that is particularly preferably used in the present invention, more specific explanation will be made in the item 3. below.

As described above, when a specimen preserving a structure in a living body is used, it is possible to morphologically verify localization of the biological molecule which is an object of mass spectrometry as same as that in the living body. That is, mass spectrometric imaging that detects a target biological molecule by mass spectrometry while keeping positional information in a living body is enabled.

[1-3. Support]

The sample to be analyzed may be held on an appropriate support. Since the present invention is directed to mass spectrometry, the one having electric conductivity may be used as a support. As such an electrically conductive support, for example, a sample plate for mass spectrometry, which is a metallic support is often used, however, a support coated with an electrically conductive substance may also be used without limited to the above. In this case, the material of the coated support is not particularly limited, and concretely those exemplified above. The electrically conductive substance is not particularly limited, and concrete examples include indium tin oxide (ITO) and the like. More concrete examples of a support coated with an electrically conductive substance include indium tin oxide-coated slide glass, and indium tin oxide-coated sheet.

The sample to be analyzed may be used so as to be held on a surface of such a electrically conductive support by sticking, or so as to be transferred to a resin support, e.g. a membrane, and then held on an electrically conductive support by bonded or the like. For holding, fixation using an electrically conductive double-sided adhesive tape may be conducted. When the electrically conductive support itself is in the form of a sheet, the electrically conductive sheet on which the sample to be analyzed is held may further be used while it is stuck on a support such as a plate.

In the present invention, it is particularly preferred that a sample to be analyzed is held on a surface of an electrically conductive support.

2. Matrix

[2-1. High concentration DHB Solution]

In the method of preparing a sample for matrix-assisted laser desorption/ionization (MALDI) mass spectrometry of the present invention, 2,5-dihydroxybenzoic acid (DHB) is used as a matrix. Though DHB is matrix that is broadly used by a person skilled in the art heretofore, DHB is used in a higher concentration than that in conventional cases. For example, it may be 40 mg/mL to saturated concentration, and more preferably about 50 mg/mL. Below this range, uniformly deposited crystals tend to be difficult to generate.

The above saturated concentration is a saturated concentration at the temperature in the operation environment. The operation environment is a temperature which is generally so-called room temperature, concretely 15 to 30° C., and preferably 20 to 25° C.

The matrix DHB is used in the form of a matrix solution by dissolving it in an appropriate solvent. The solvent and its composition for dissolving the matrix may be appropriately determined by a person skilled in the art, and an aqueous solution of acetonitrile (ACN)-trifluoroacetic acid (TFA) is often used. Composition of the aqueous solution of acetonitrile (ACN)-trifluoroacetic acid (TFA) may be determined appropriately by a person skilled in the art. For example, it may be an aqueous solution containing 25 to 50(v/v) % ACN-0.05 to 1 (v/v) % TFA.

[2-2. Means for Dispensing]

A DHB solution of such high concentration is supplied to the biological sample with a matrix using a dispenser equipped with an inkjet mechanism. As to the dispenser equipped with an inkjet mechanism, a mechanism utilizing a piezo element or the like is recited, and such a dispenser, a chemical printer CHIP-1000 (made by SHIMADZU CORPORATION) or the like may be recited.

A dispenser equipped with an inkjet mechanism is able to dispense liquid droplets of a picoliter order to a microscopic region. Concretely, an amount of a reagent that is dispensed at one discharge may be controlled to, for example, about 100 pL, and however, it may be an even smaller amount depending on the mechanism of the inkjet. For example, discharge of about 100 pL produces a minimum dispensing range of about 100 μm in a diameter.

When DHB is prepared in a high concentration, and dispensed into a microscopic region by an inkjet technique, uniformly deposited crystals generate. Crystals may be produced by overlaying the DHB solution in the same site. When dispensing is conducted in such an overlaying manner, overlaying may be conducted about 5 to 80 times, preferably 15 to 40 times, for each site.

Crystals in a minute region may be generated in a section specimen of a biological sample (concretely, a frozen section or a biological sample derived from a paraffin section). Further, among the section specimens, a biological sample from a paraffin section tends to form crystals more easily in a microscopic region compared to a frozen section because liquid droplet are less likely to extend.

In MALDI mass spectrometry, preparing the preferable crystals to cause effective ionization of molecule to be measured is a factor that is greatly involved in quality of an analysis (for example, quantitative performance and reproducibility). As in the present invention, dispensing a high concentration DHB solution by an inkjet technique allows production of a crystal in which a matrix is uniformly deposited, which is preferable for effective ionization of a molecule to be measured. Therefore, it is preferable in that a mass spectrum having excellent quantitative performance and reproducibility can be obtained. Furthermore, this point is particularly important in an automatic analysis. Additionally, unlike α-cyano-hydroxycinnamic acid and the like, DHB is less likely to get clogged in an inkjet nozzle even with a solution with a high concentration. Therefore, dispensing the high concentration DHB solution by the inkjet technique is preferred also in the point of excellent workability.

[2-3. Dispensing Pitch]

When using the specimen of the biological sample section as a sample to be analyzed in the present invention, by two-dimensionally conducting the above dispensing operation over a certain range of the biological sample, it is possible to achieve imaging based on a distribution of a targeted biological molecule on mass, namely mass spectrometric imaging. Since the bioimaging technique using mass spectrometry identifies a biological molecule itself, it is possible to directly grasp a biological molecule based on the quantification result. On the other hand, the bioimaging technique using microscopy grasps a biological molecule indirectly. Therefore, the mass spectrometric imaging is superior in the point that accuracy of an analytical result is greater.

Figure 11:
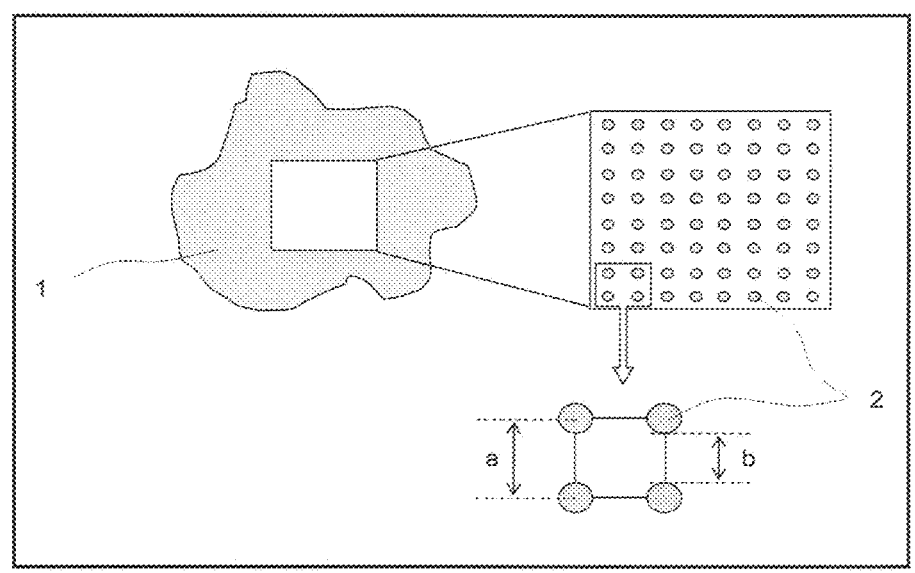
FIG. 11 is a schematic view showing the appearance that matrix is two-dimensionally dispensed on a biological sample.

Here, FIG. 11 shows a schematic view of a biological sample 1 and a crystal (or a liquid droplet) of matrix 2. For example, at the same dispensing pitch a, the larger the diameter of a crystal (or a liquid droplet), the narrower the interval b between crystals (or a liquid droplets) becomes. At the same crystal (or a liquid droplets) diameter, the smaller the dispensing pitch a, the narrower the interval b between crystals (or a liquid droplet) is. A plurality of matrix crystals arranged in the vertical and horizontal directions in FIG. 11 are formed on the sample. For achieving this, dispensing may be repeated for every site or dispensing for plural sites at once by using a means having a plurality of inkjet nozzles.

In the present invention, it is possible to produce crystals in which the matrix is uniformly deposited at any position on the biological sample, by appropriately setting a dispensing pitch. Such a dispensing pitch is 100 to 200 μm, more preferably 125 to 200 μm, and further preferably 150 to 175 μm. In the present invention, the vertical and horizontal pitches in FIG. 11 may be set within such a range. Below the above range, an interval between liquid droplets tends to be too narrow, and the liquid droplets dropped by the dispensing operation tend to associate to become a large liquid droplet, so that a non-uniform crystal tends to generate. Over the above range, the crystal distribution tends to be too sparse and the area where ionization does not occur by laser irradiation in measurement tends to increase, so that an analytical result of a small information amount tends to be obtained.

By selecting the above dispensing pitch, it is possible to ionize the biological molecule to be measured on the biological sample evenly and effectively, and to find the localization as well as the precise positional information. This will be very useful when the method of the present invention is intended, for example, for an analysis of brain having an especially complicated structure.

When matrix dispensing according to a conventional method is conducted, an operation of visually checking the part where uniform crystals generate with a CCD camera or the like, and irradiating the checked position with a laser beam is often executed. However in the present invention, since high concentration DHB is dispensed at a pitch as described above, it becomes possible to produce crystals in which a matrix is uniformly deposited in any position on the biological sample.

[2-4. Mass Spectrometer]

As a mass spectrometer used in the present invention, a matrix-assisted laser desorption/ionization (MALDI) mass spectrometer is preferred. For example, as an apparatus that is preferred from the point of capability of second or higher order of multi-stage MS analysis, AXIMA-QIT (made by SHIMADZU CORPORATION) is exemplified. By using a mass spectrometer capable of second or higher order of multi-stage MS analysis, it is possible to identify a measured molecule.

In the following, the case of using a paraffin-embedded specimen (item 3.) which is a preferred embodiment of the present invention, the case of executing a digestion treatment (item 4.), and the case of executing a hydration treatment (item 5.) will be further explained as a supplement.

3. Paraffin-Embedded Specimen

[3-1. Paraffin]

Also as a paraffin-embedded specimen in the present invention, specimens that are to become research targets in any analyses including morphologic, immunohistochemical, and enzymehistochemical analyses are intended, as well as a specimen by other embedding media. In many cases, it is a sliced specimen of a formalin-fixed and paraffin-embedded (FFPE) biological sample. Paraffin in the present invention embraces those used as embedding media in such any analyses.

One example of a paraffin-embedded specimen in the present invention is a specimen prepared by using a petroleum-based paraffin wax alone as an embedding medium. Here, the petroleum-based wax refers to a mixture of hydrocarbons that are derived from petroleum and are solid at normal temperature. Further, the term hydrocarbons normally means saturated hydrocarbons having a molecular weight of about 300 to 500 which comprises linear hydrocarbons (normal paraffins) with an average carbon number of about 20 to 35 as a main component.

Another example of paraffin-embedded specimen according to the present invention is a specimen prepared by using an embedding medium containing the above-described petroleum-based paraffin wax as a base and further containing additional ingredients. As such additional ingredients, any ingredient that may be added for the purpose of improving quality of the embedding medium or the like are accepted. As an example of an embedding medium in which the additional ingredients are blended, an embedding medium in which a petroleum-based microcrystalline wax, polyisobutylene, an ethylene-vinyl acetate copolymer and polybutene are blended as the additional ingredients for the purpose of improving workability in slicing and cracking resistance at low temperature (for example, Japanese Patent Application Laid-Open Publication No. 2002-107354); an embedding medium in which polyisobutylene, an ethylene-vinyl acetate copolymer and saturated fatty acid are blended as the additional ingredients for the purpose of lowering the melting point, and improving workability in slicing and cracking resistance at low temperature (for example, Japanese Patent Application Laid-Open Publication No. 2004-212391) and the like are recited.

A melting point of the paraffin used in a paraffin-embedded specimen of the present invention is, for example, about 45 to 70° C. (value measured in conformance with JIS K-2235), though it depends on its ingredients and composition.

[3-2. Deparaffinization Treatment]

A deparaffinization treatment method of a paraffin-embedded specimen is not particularly limited, and may be conducted appropriately by a person skilled in the art. For example, it may be achieved by an operation of subjecting a paraffin-embedded specimen to an organic solvent that is compatible to the paraffin and dissolving the paraffin in the organic solvent under a normal temperature condition. Typically, this operation is repeated plural times (for example, about twice to four times).

Besides the deparaffinization treatment method that is conventionally conducted as described above, a heating-deparaffinization method developed by the inventors of the present application is more preferably used. In a heating-deparaffinization method, a paraffin-embedded specimen is subjected to an organic solvent having compatibility to the paraffin under heating condition, to effect melting and dissolution to an organic solvent of paraffin.

[3-2-1. Organic Solvent]

As the organic solvent, any organic solvents that are compatible with paraffin, more concretely, any organic solvents may be used without any limitation insofar as they exhibit solubility of such an extent that will not cause phase separation with paraffin. For example, an organic solvent which is used as an intermediate agent for replacing for a dehydrating agent in a biological sample may be used after replacing water in the biological sample with a dehydrating agent, and before permeation of paraffin in the biological sample, in an embedding operation with paraffin. An example of organic solvent in the present invention may be selected from xylene, chloroform, diethyl ether, lemosol, and alcohols (for example, methanol, isopropyl alcohol and the like). These organic solvents may be used solely or in mixture of two or more kinds.

[3-2-2. Heating Deparaffinization Treatment]

A deparaffinization treatment method conventionally conducted has been approved in common-sense manner because it satisfies an immunohistochemically significant analytical result, it may not be said that the method is approved similarly in a mass spectrometric approach. As one reason, when mass spectrometry is used, the influence of paraffin remaining in a biological sample on an analytical result is considered to be larger than influence in microscopy. That is, the remaining paraffin will cause a mass spectrum of a small amount of information regarding a target biological molecule, and will exert an adverse affect on quality of the analysis.

The method for heating-deparaffinization of the present invention comprises the steps of: exposing a biological sample by subjecting a specimen in which the biological sample is embedded in paraffin, to an organic solvent that is compatible with the paraffin under heating condition, to make the paraffin be melted and dissolved in the organic solvent; and removing the paraffin from the specimen by separating the organic solvent dissolving the paraffin, from the exposed biological sample. The above two steps may be conducted stepwise, or at once. Concrete examples of operation will be described below.

For example, such an operation may be carried out that in the step of exposing a biological sample, the specimen in which the biological sample is embedded in paraffin is immersed and retained in the organic solvent which is heated, and then in the step of removing paraffin, the specimen retained in the organic solvent is drawn up from the organic solvent.

In this example, before immersing the paraffin-embedded specimen in the heated organic solvent, the paraffin-embedded specimen may be heated in advance to melt the paraffin.

Further, the heated organic solvent may be prepared by heating the organic solvent using a warm water bath.

Also such an operation may be conducted that, in the step of exposing the biological sample, the specimen in which the biological sample is embedded in paraffin is immersed in the organic solvent, and temperature of the organic solvent is raised and retained at an appropriate temperature; and then in the step of removing paraffin, the specimen retained in the organic solvent is drawn up from the organic solvent.

In the heating-deparaffinization, since elution of paraffin is effectively conducted, it is typically sufficient to conduct the operation comprising immersion into the organic solvent and drawing up only once. The operation may be conducted plural times in consideration of the heating temperature.

Furthermore, for example, the step of exposing the biological sample and the step of removing paraffin may be conducted at once by continuously applying a heated organic solvent onto the specimen in which the biological sample is embedded in paraffin.

In this example, before applying the heated organic solvent on the paraffin-embedded specimen, the paraffin-embedded specimen may be heated in advance to melt paraffin. The heated organic solvent may be prepared by heating the organic solvent by using a warm water bath.

Furthermore, after conducting the operation as exemplified above, further washing may be conducted by immersing and retaining in a warmed organic solvent (with no dissolved paraffin) or applying the warmed organic solvent, whereby the step of removing the paraffin may be conducted more strictly.

In the heating-deparaffinization, a heating condition or a temperature control condition is defined as a temperature condition around the melting point of paraffin. By applying such a temperature setting, it is possible to cause occurrence of a melting phenomenon of paraffin itself, so that it is possible to make the melted paraffin be dissolved (compatible) in the organic solvent. It is considered that this may make it possible to remove the paraffin having permeated in the biological sample more efficiently compared to the conventional method wherein solid paraffin is dissolved in an organic solvent. That is, the biological sample embedded in the paraffin is exposed more preferably compared to conventional cases. Therefore, the influence of remaining paraffin is smaller than those in conventional cases in later analysis of biological sample. This appears as a particularly good result when mass spectrometry is used in an analysis of a subsequent analysis of a biological sample.

A concrete heating temperature is not particularly limited because a melting point differs depending on the kinds of paraffin, and may be determined appropriately by a person skilled in the art. For example, as described above, since melting point of paraffin is, for example, about 45 to 70° C., the heating condition may also be 45 to 70° C. There is also the case that 55 to 65° C. is preferred. Examples demonstrated that a mass spectrum of abundant information amount can be obtained when the deparaffinization treatment according to the heating-deparaffinization is conducted at a heating condition of 55 to 65° C., and then the specimen having subjected to the deparaffinization treatment is subjected to mass spectrometry. Below the above range, efficient melting of paraffin tends not to occur, and sufficient deparaffinization tends not to occur, so that a mass spectrum of a poor information amount tends to be obtained, whereas over the above range, a damage of a biological sample itself tends to be more likely to occur.

As for the heating time, there is no particular limitation, and determination may be made by a person skilled in the art appropriately in consideration of a heating temperature, an embedding substance and the like various factors. For example, it may be about 5 to 20 minutes, and more preferably about 10 to 15 minutes. There are some cases that, under a temperature condition of about 60° C., about 10 to 15 minutes may be particularly preferred. Below the above range, sufficient deparaffinization tends not to occur, and a mass spectrum of a poor information amount tends to be obtained, whereas over the above range, a damage of a biological sample itself tends to be more likely to occur.

[3-2-3. Biological Sample Having Subjected to Deparaffinization Treatment]

Since paraffin is removed from the paraffin-embedded specimen by deparaffinization treatment, the resultant biological sample is exposed. Especially, since paraffin is more effectively removed from the paraffin-embedded specimen by the heating-deparaffinization method, the resultant biological sample is better exposed. There is a possibility that a heating condition in the heating-deparaffinization treatment provides the biological sample obtained by the treatment with not only a physically preferable effect such as exposure of a biological sample but also other, for example, a biochemically preferable effect.

Furthermore, when the heating-deparaffinization treatment is conducted, the used organic solvent vaporizes effectively by the heating condition. Therefore, unlike a biological sample obtained by a conventional method for deparaffinization, in a biological specimen obtained by the method for heating-deparaffinization, an organic solvent is effectively removed. Therefore, in the case that treatments such as a dying treatment and a digestion treatment using an aqueous reagent is conducted, prior to such treatments a hydration treatment that is typically conducted in conventional arts is not necessarily required. Thus, the heating condition in the deparaffinization treatment of the present invention provides a preferred effect from the viewpoint of workability of the biological sample obtained by the treatment.

A biological sample obtained through the deparaffinization of the present invention may be subjected to any type of analysis. For example, DNA analysis, mRNA analysis, protein analysis and the like may be recited. As methods of these analyses, approaches may be made from any points of view including morphological, immunohistochemical, and enzymehistochemical approaches.

When a biological sample that is obtained while conducting the method for deparaffinization is subjected to analysis, a pretreatment for the analysis is further conducted appropriately as needed by a person skilled in the art. As such a process, for example, a digestion treatment and a hydration treatment are recited.

In particular, when a biological molecule such as protein is analyzed by using mass spectrometry, the method for heating-deparaffinization is useful as a pretreatment method. In such a method for an analysis, a hydration step and/or a digestion step may further be conducted between the deparaffinization step and the mass spectrometry step. When both of a hydration step and a digestion step are conducted, the digestion step is conducted after the hydration step.

4. Hydration Treatment

When a hydration treatment is executed, concrete operation thereof and various conditions may be determined appropriately by a person skilled in the art. Typically, an organic solvent that is compatible with both the organic solvent used in the above deparaffinization (namely, the organic solvent that is compatible with paraffin) and water is used. As such an organic solvent for the hydration treatment, the alcohol is used in most cases. Concretely, by using an organic solvent for the hydration treatment, followed by aqueous solutions in which the organic solvent is serially diluted, a biological sample may be hydrated.

Also for the biological sample obtained by conducting heating-deparaffinization, by conducting such a hydration treatment, the organic solvent for deparaffinization that remains unvaporized to remain in the biological sample is effectively washed off. Therefore, when a biological sample is subjected to mass spectrometry, more peaks originating from a target biological molecule can be obtained.

5. Digestion Treatment

When a digestion treatment is executed, concrete operation thereof and various conditions may be determined appropriately by a person skilled in the art. For example, a solution of protease such as trypsin may be added and incubated in a wet condition.

By conducting such a digestion treatment, it is possible to obtain a mass spectrum containing more peaks originating from a target biological molecule when a biological sample is subjected to mass spectrometry. Concretely, a mass spectrum, having at least the information amount that is obtainable when mass spectrometry is conducted on a frozen section having subjected to a digestion treatment, is ensured.

In the digestion step, as a method of supplying a regent with a biological sample, dispensing (namely, supplying liquid drop of minute amount) may be conducted. The dispensing operation makes it possible to supply a microscopic region of the biological sample with the reagent. For conducting the dispensing, any device capable of supplying a minute amount of the reagent solution may be used without any particular limitation. In particular, a dispenser equipped with an inkjet mechanism is preferably used. As a concrete inkjet mechanism, a mechanism using a piezoelectric element or the like is recited. As such a dispensing device, a chemical printer CHIP-1000 (made by SHIMADZU CORPORATION) or the like is recited.

EXAMPLES

In the following, the present invention will be explained in detail by way of Examples. However, the present invention will not be limited to these Examples. In the following, an amount represented in % is an amount based on volume unless otherwise specified.

Example 1

Preparation of Matrix Crystal in Biological Sample Section

A 10 μm-thick section was prepared from a paraffin block of a mouse brain by means of a microtome, stuck on an indium tin oxide coated slide glass 8-12 ohms (Aldrich), and extended and dried by an extender (50° C., 1 hour). A dying pot accommodating xylene was warmed in advance in a water bath, and a dry paraffin section was put into the dying pot when the temperature of xylene reached 60° C., and left still for 10 minutes. As the hydration treatment, after conducting a 100% ethanol treatment of 5 minutes twice, 90% ethanol treatment of 5 minutes, 80% ethanol treatment of 5 minutes and 70% ethanol treatment of 5 minutes at room temperature, the section was dried in a desiccator.

A matrix crystal was prepared on a section obtained, in the following manner. A 50 mg/mL of 2,5-dihydroxybenzoic acid solution was prepared using a 50% acetonitrile-0.1% trifluoroacetic acid aqueous solution as a solvent. The prepared high concentration matrix solution was added dropwise on a deparaffinized section using a micro pipette. A photograph of the resultant crystal is shown in FIG. 1(a). Further, the prepared high concentration matrix solution was added dropwise on a deparaffinized section using a chemical printer CHIP-1000 (SHIMADZU CORPORATION). A photograph of the resultant crystal is shown in FIG. 1(b).

10 mg/mL of a 2,5-dihydroxybenzoic acid solution was prepared using a 50% acetonitrile-0.1% trifluoroacetic acid aqueous solution as a solvent. The prepared low concentration matrix solution was added dropwise on a deparaffinized section using a chemical printer CHIP-1000. A photograph of the resultant crystal is shown in FIG. 2(a). Taking a notice of the part surrounded by the circle, for example, it can be found that the crystals generate unevenly.

FIG. 2(b) is a crystal obtained by dropping the above 50 mg/mL high concentration matrix solution on a deparaffinized section using a chemical printer CHIP-1.000, and is a part of the above FIG. 1(b) enlarged to the same scale as FIG. 2(a).

These photographs demonstrate that by dropping the high concentration matrix solution by an inkjet mechanism, uniform crystals generate evenly.

Example 2

Mass Spectrometry from Paraffin Section Using Conventional Method for Deparaffinization A 10 μm-thick section was prepared from a paraffin block of a mouse brain by means of a microtome, stuck on an indium tin oxide coated slide glass 8-12 ohms (Aldrich), and extended and dried by an extender (50° C., 1 hour). As a conventional deparaffinization treatment, a 100% xylene treatment of 5 minutes was conducted three times. Subsequently, after conducting a 100% ethanol treatment of 5 minutes twice, 90% ethanol treatment of 5 minutes, 80% ethanol treatment of 5 minutes and 70% ethanol treatment of 5 minutes at room temperature as a hydration treatment, the section was dried in a desiccator.

To the obtained deparaffinized section, 100 μg/mL trypsin (in 10 mM $NaHCO_3$ aqueous solution) was dispensed with the use of CHIP-1000 (SHIMADZU CORPORATION), and allowed to react for 3 hours in an incubator at 37° C. Next, on the section, 50 mg/mL DHB (Wako Pure Chemical Industries, Ltd.) (in 50% acetonitrile-0.1% trifluoroacetic acid aqueous solution) was dispensed and overlaid at a pitch of 150 μm using a CHIP-1000. Concretely, 5 droplets×15 cycles for 1 spot, a total of 7500 pL was dispensed and overlaid. As an index, Bradykinin (1 pmol/1.5 mm×1.5 mm) was contained in the DHB solution. Subsequently, measurement by an AXIMA-QIT (made by SHIMADZU CORPORATION) was conducted under the condition of 100 spots of 450 μm×450 μm at a pitch of 50 μm, 2 profiles for each spot, and a total of 200 profiles. Peak picking of the result was conducted by a Mascot Distiller (Matrix Science, Ltd.)

Example 3

Mass Spectrometry from Paraffin Section Using Method for Heating-Deparaffinization (Heating Time: 10 Minutes)

A 10 μm-thick section was prepared from a paraffin block of a mouse brain by means of a microtome, stuck on an indium tin oxide coated slide glass 8-12 ohms (Aldrich), and extended and dried by an extender (50° C., 1 hour). A dying pot accommodating xylene was warmed in advance in a water bath, and a dry paraffin section was put into the dying pot when the temperature of xylene reached a temperature determined as an examination condition, and left still for 10 minutes. As the temperature of xylene, the conditions of 55° C., 60° C., and 65° C. were examined. Next, as the hydration treatment, after conducting a 100% ethanol treatment of 5 minutes twice, 90% ethanol treatment of 5 minutes, 80% ethanol treatment of 5 minutes and 70% ethanol treatment of 5 minutes at room temperature, the section was dried in a desiccator.

To the obtained deparaffinized section, 100 μg/mL trypsin (in 10 mM $NaHCO_3$ aqueous solution) was dispensed with the use of CHIP-1000 (SHIMADZU CORPORATION), and allowed to react for 3 hours in an incubator at 37° C. Next, on the section, 50 mg/mL DHB (Wako Pure Chemical Industries, Ltd.) (in 50% acetonitrile-0.1% trifluoroacetic acid aqueous solution) was dispensed and overlaid at a pitch of 150 μm using a CHIP-1000. Concretely, 5 droplets×15 cycles for 1 spot, a total of 7500 pL was dispensed and overlaid. As an index, Bradykinin (1 pmol/1.5 mm×1.5 mm) was contained in the DHB solution. Subsequently, measurement by an AXIMA-QIT (made by SHIMADZU CORPORATION) was conducted under the condition of 100 spots of 450 μm×450 μm at a pitch of 50 μm, 2 profiles for each spot, and a total of 200 profiles. Peak picking of the result was conducted by a Mascot Distiller (Matrix Science, Ltd.)

Figure 3:
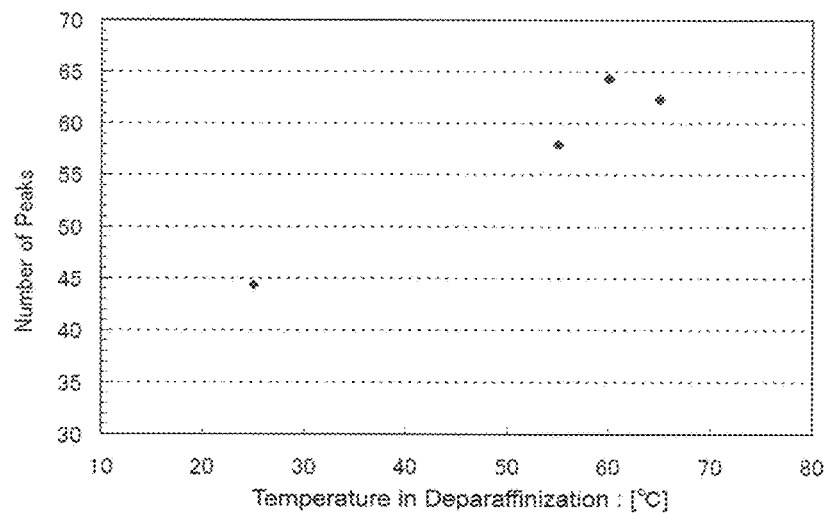
FIG. 3 is a graph showing a result of mass spectrometry from a paraffin section using a conventional method for deparaffinization (Example 2), and a result of mass spectrometry from a paraffin section using a method for heating-deparaffinization (heating time: 10 min.) (Example 3) in the form of relation between a temperature at the time of deparaffinization and the number of peaks in mass spectrum.

[FIG. 3: Examination of Temperature Condition of Deparaffinization]

FIG. 3 shows results of the above Example 2 and Example 3. Concretely, FIG. 3 is a graph showing a result of mass spectrometry from a paraffin section using a conventional method for deparaffinization (Example 2), and a result of mass spectrometry from a paraffin section using a method for deparaffinization (heating time: 10 min.) according to the present invention (Example 3) in the form of relation between a temperature at the time of deparaffinization and the number of peaks in mass spectrum. In FIG. 3, the horizontal axis represents temperature (° C.) at the time of deparaffinization, and the vertical axis represents the number of peaks. These results demonstrate that a larger number of peaks were detected by conducting heating.

Example 4

Mass Spectrometry from Paraffin Section Using Method For Heating-Deparaffinization (Heating Temperature: 60° C.)

A 10 μm-thick section was prepared from a paraffin block of a mouse brain by means of a microtome, stuck on an indium tin oxide-coated slide glass 8-12 ohms (Aldrich), and extended and dried by an extender (50° C., 1 hour). A dying pot accommodating xylene was warmed in advance in a water bath, and a dry paraffin section was put into the dying pot when the temperature of xylene reached 60° C., and left still. As the heating time, the conditions of 5 min, 10 min, and 15 min were examined. Next, as the hydration treatment, after conducting a 100% ethanol treatment of 5 minutes twice, 90% ethanol treatment of 5 minutes, 80% ethanol treatment of 5 minutes and 70% ethanol treatment of 5 minutes at room temperature, the section was dried in a desiccator.

To the obtained deparaffinized section, 100 μg/mL trypsin (in 10 mM $NaHCO_3$ aqueous solution) was dispensed with the use of CHIP-1000 (SHIMADZU CORPORATION), and allowed to react for 3 hours in an incubator at 37° C. Next, on the section, 50 mg/mL DHB (Wako Pure Chemical Industries, Ltd.) (in 50% acetonitrile-0.1% trifluoroacetic acid aqueous solution) was dispensed and overlaid at a pitch of 150 μm using a CHIP-1000. Concretely, 5 droplets×15 cycles for 1 spot, a total of 7500 pL was dispensed and overlaid. As an index, Bradykinin (1 pmol/1.5 mm×1.5 mm) was contained in the DHB solution. Subsequently, measurement by an AXIMA-QIT (made by SHIMADZU CORPORATION) was conducted under the condition of 100 spots of 450 μm×450 μm at a pitch of 50 μm, 2 profiles for each spot, and a total of 200 profiles. Peak picking of the result was conducted by a Mascot Distiller (Matrix Science, Ltd.)

Figure 4:
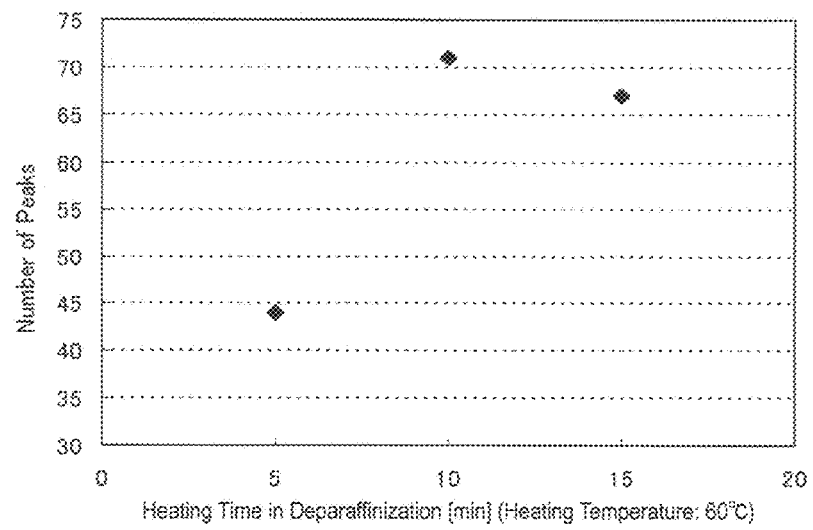
FIG. 4 is a graph showing a result of mass spectrometry from a paraffin section using a method for heating-deparaffinization (heating temperature: 60° C.) according to the present invention (Example 4) in the form of relation between a heating time at the time of deparaffinization and the number of peaks in mass spectrum.

[FIG. 4: Examination of Time Condition of Deparaffinization]

FIG. 4 shows a result of the above Example 4. Concretely, FIG. 4 is a graph showing a result of mass spectrometry from a paraffin section using a method for deparaffinization (heating temperature: 60° C.) according to the present invention (Example 4) in the form of relation between a heating time at the time of deparaffinization and the number of peaks in mass spectrum. In FIG. 4, the horizontal axis represents heating time (min.) at the time of deparaffinization, and the vertical axis represents the number of peaks.

Example 5

Mass Spectrometry from Paraffin Section Using Method for Deparaffinization (Heating Condition: 60° C.—10 Min.) of the Present Invention A 10 μm-thick section was prepared from a paraffin block of a mouse brain by means of a microtome, stuck on an indium tin oxide coated slide glass 8-12 ohms (Aldrich), and extended and dried by an extender (50° C., 1 hour). A dying pot accommodating xylene was warmed in advance in a water bath, and a dry paraffin section was put into the dying pot when the temperature of xylene reached 60° C., and left still for 10 minutes. As the hydration treatment, after conducting a 100% ethanol treatment of 5 minutes twice, 90% ethanol treatment of 5 minutes, 80% ethanol treatment of 5 minutes and 70% ethanol treatment of 5 minutes at room temperature, the section was dried in a desiccator.

To the obtained deparaffinized section, 100 μg/mL trypsin (in 10 mM $NaHCO_3$ aqueous solution) was dispensed with the use of CHIP-1000 (SHIMADZU CORPORATION), and allowed to react for 3 hours in an incubator at 37° C. Next, on the section, 50 mg/mL DHB (Wako Pure Chemical Industries, Ltd.) (in 50% acetonitrile-0.1% trifluoroacetic acid aqueous solution) was dispensed and overlaid at a pitch determined as an examination condition using a CHIP-1000. Concretely, 5 droplets×15 cycles for 1 spot, a total of 7500 pL was dispensed and overlaid. As the dispensing pitch, the conditions of 200 μm, 175 μm, 150 μm, 125 μm and 100 μm were examined. As an index, Bradykinin (1 pmol/1.5 mm×1.5 mm) was contained in the DHB solution. Subsequently, measurement by an AXIMA-QIT (made by SHIMADZU CORPORATION) was conducted under the condition of 100 spots of 450 μm×450 μm at a pitch of 50 μm, 2 profiles for each spot, and a total of 200 profiles. Peak picking of the result was conducted by a Mascot Distiller (Matrix Science, Ltd.)

[FIG. 5: Examination Of Dispensing Pitch]

FIG. 5 shows a result of the above Example 5. Concretely, FIG. 5 is a graph showing a result of mass spectrometry from a paraffin section using a method for deparaffinization (heating condition: 60° C.—10 min.) according to the present invention (Example 5), in the form of relation between a dispensing pitch of a matrix solution and the number of peaks in mass spectrum. In FIG. 5, the horizontal axis represents a dispensing pitch (μm) and the vertical axis represents the number of peaks.

Example 6

Mass Spectrometry from Paraffin Section Using Inventive Method for Analysis (Deparaffinization: 60° C.—10 Min.) not Executing Hydration Treatment A 10 μm-thick section was prepared from a paraffin block of a mouse brain by means of a microtome, stuck on an indium tin oxide coated slide glass 8-12 ohms (Aldrich), and extended and dried by an extender (50° C., 1 hour). A dying pot accommodating xylene was warmed in advance in a water bath, and a dry paraffin section was put into the dying pot when the temperature of xylene reached 60° C., and left still for 10 minutes. The paraffin section was put out from the pot, and xylene was vaporized.

To the obtained deparaffinized section, 100 μg/mL trypsin (in 10 mM $NaHCO_3$ aqueous solution) was dispensed with the use of CHIP-1000 (SHIMADZU CORPORATION), and allowed to react for 3 hours in an incubator at 37° C. Next, on the section, 50 mg/mL DHB (Wako Pure Chemical Industries, Ltd.) (in 50% acetonitrile-0.1% trifluoroacetic acid aqueous solution) was dispensed and overlaid at a pitch determined as an examination condition using a CHIP-1000. Concretely, 5 droplets×15 cycles for 1 spot, a total of 7500 pL was dispensed and overlaid. As the dispensing pitch, the conditions of 200 μm, 175 μm, 150 μm, 125 μm and 100 μm were examined. As an index, Bradykinin (1 pmol/1.5 mm×1.5 mm) was contained in the DHB solution. Subsequently, measurement by an AXIMA-QIT (made by SHIMADZU CORPORATION) was conducted under the condition of 100 spots of 450 μm×450 μm at a pitch of 50 μm, 2 profiles for each spot, and a total of 200 profiles. Peak picking of the result was conducted by a Mascot Distiller (Matrix Science, Ltd.)

[FIG. 6: Comparison and Examination of Presence/Absence Of Hydration Treatment]

FIG. 6 shows a result of above Example 6, together with a result corresponding to Example 5 (namely, the result obtained by separately conducting the same operation as Example 5). FIG. 6 is a graph showing a result of mass spectrometry from a paraffin section according to a method for an analysis of the present invention in which a hydration treatment is conducted (deparaffinization condition: 60° C.—10 min.) (Example 5) and a result of mass spectrometry from a paraffin section according to a method for an analysis of the present invention in which a hydration treatment is not conducted (deparaffinization condition: 60° C.—10 min.) (Example 6), in the form of relation between a dispensing pitch of a matrix solution and the number of peaks in mass spectrum. In FIG. 6, the horizontal axis represents a dispensing pitch (μm), and the vertical axis represents the number of peaks.

Example 7

Mass Spectrometry from Frozen Section

A 10 μm-thick section was prepared from a frozen block of a mouse brain by means of a cryostat, stuck on an indium tin oxide coated slide glass 8-12 ohms (Aldrich), and dried in air. After a treatment with 70% ethanol for 5 minutes at room temperature, the section was dried in a desiccator.

To the frozen section, 100 μg/mL trypsin (in 10 mM $NaHCO_3$ aqueous solution) was dispensed with the use of CHIP-1000 (SHIMADZU CORPORATION), and allowed to react for 3 hours in an incubator at 37° C. Next, on the section, 50 mg/mL DHB (Wako Pure Chemical Industries, Ltd.) (in 50% acetonitrile-0.1% trifluoroacetic acid aqueous solution) was dispensed and overlaid at a pitch of 150 μm using a CHIP-1000. Concretely, 5 droplets×15 cycles for 1 spot, a total of 7500 pL was dispensed and overlaid. As an index, Bradykinin (1 pmol/1.5 mm×1.5 mm) was contained in the DHB solution. Subsequently, measurement by an AXIMA-QIT (made by SHIMADZU CORPORATION) was conducted under the condition of 100 spots of 450 μm×450 μm at a pitch of 50 μm, 2 profiles for each spot, and a total of 200 profiles. Peak picking of the result was conducted by a Mascot Distiller (Matrix Science, Ltd.)

Figure 7:
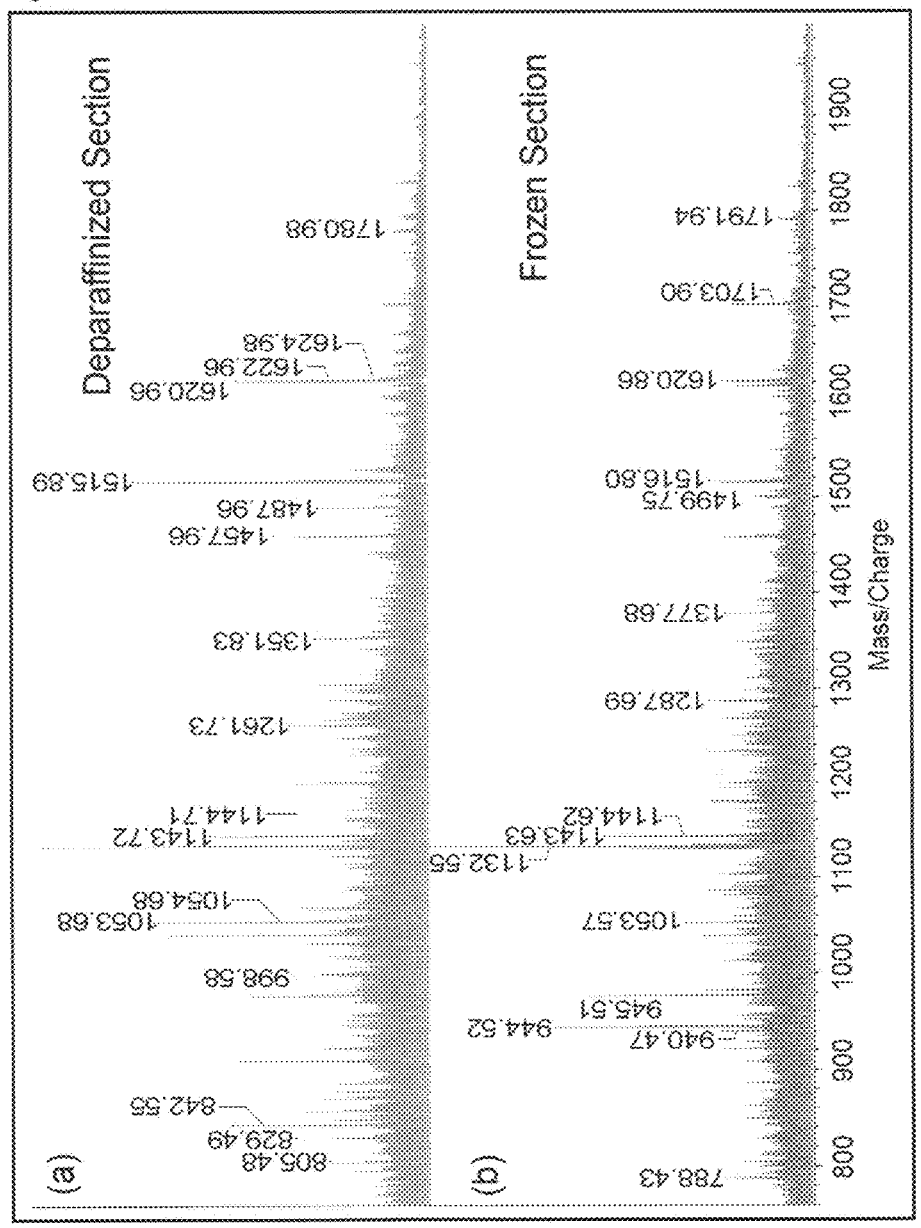
FIG. 7(a) is a mass spectrum obtained as a result of mass spectrometry from a paraffin section (Example 5: deparaffinization condition is 60° C., 10 min.)
FIG. 7(b) is a mass spectrum obtained as a result of mass spectrometry from a frozen section (Example 7)

[FIG. 7: Comparison and Examination of Mass Spectrums Obtained from Frozen Section and from Paraffin Section]

FIG. 7(*a*) is a mass spectrum obtained as a result of mass spectrometry from a paraffin section (Example 5: deparaffinization condition is 60° C., 10 min.), and FIG. 7(*b*) is a mass spectrum obtained as a result of mass spectrometry from a frozen section (Example 7). In FIG. 7(*a*) and FIG. 7(*b*), the horizontal axis represents Mass/Charge, and the vertical axis represents ionic strength. As shown in FIG. 7, according to the method of the present invention, even in the case of a sample prepared from a paraffin section, a mass spectrum of the same quality or even better quality in an information amount compared to a sample from a frozen section can be obtained.

Figure 8:
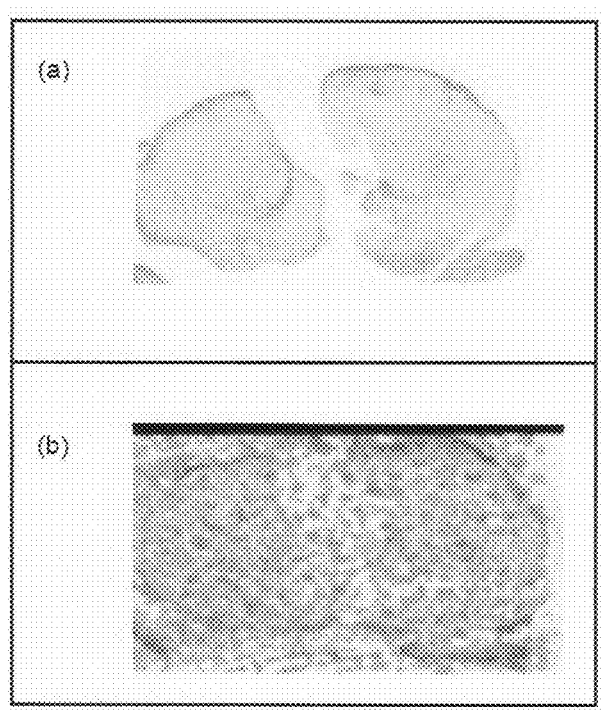
FIG. 8(a) is an actual image of a paraffin section analyzed in the present invention.
FIG. 8(b) is an actual image of a paraffin section after dispensing of a matrix.
Figure 9:
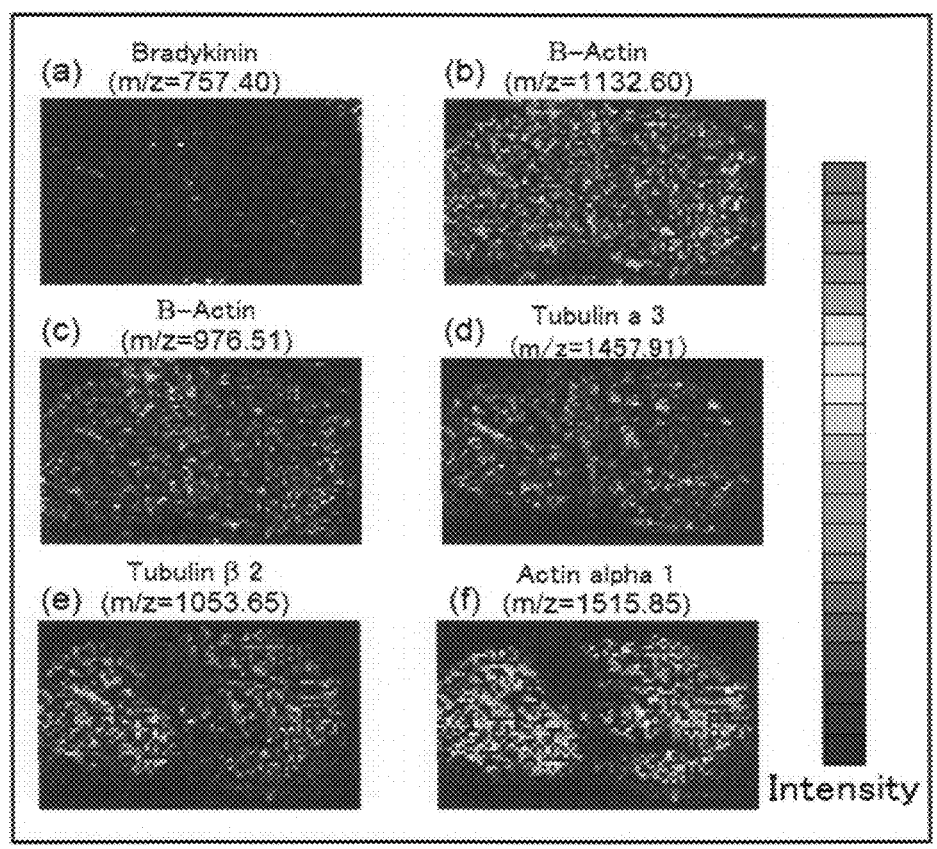
FIG. 9 shows images (a) to (f) obtained by mass spectrometric imaging of the paraffin section according to a method for analysis of the present invention (deparaffinization condition: 60° C.—10 min., hydration treatment: conducted, matrix solution dispensing pitch: 150 μm)
Figure 10:
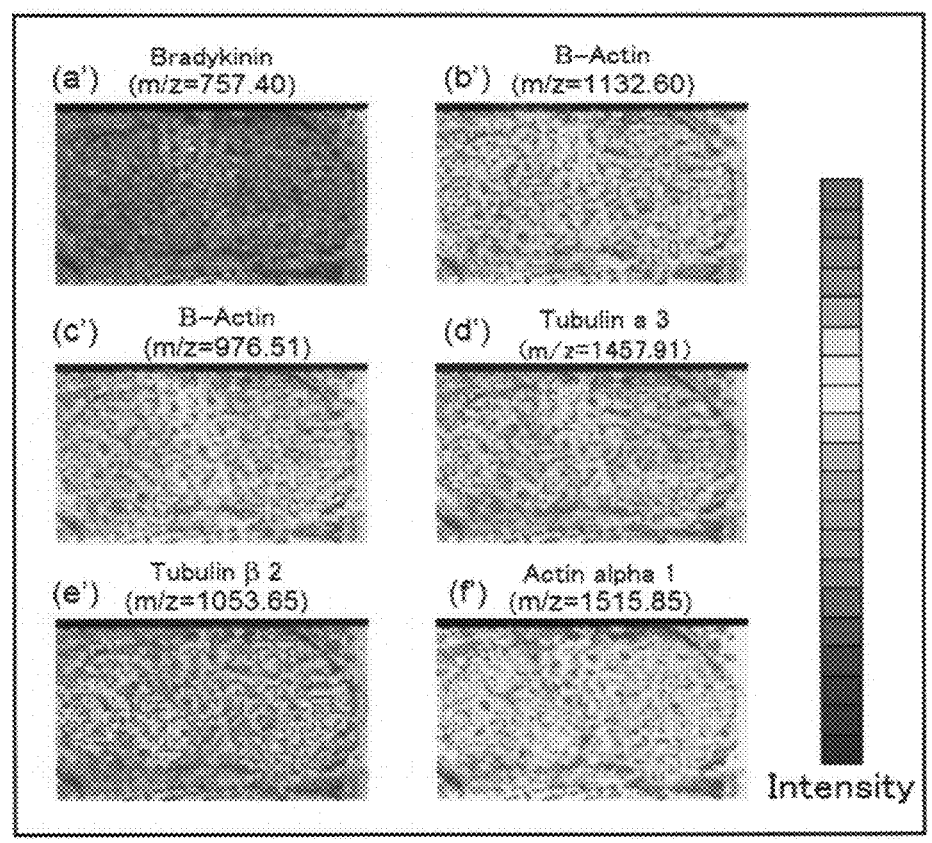
FIG. 10 shows images (a') to (f') obtained by superimposing an actual image (b) after dispensing of matrix in FIG. 8, on the images (a) to (f) of FIG. 9.

[FIGS. 8 to 10: Mass Spectrometric Imaging]

FIG. 8(*a*) shows an actual image of a paraffin section analyzed in the present invention, and FIG. 8(*b*) shows an actual image of a paraffin section after dispensing of a matrix.

FIG. 9 shows images (a) to (f) obtained by mass spectrometric imaging of the paraffin section according to a method for an analysis of the present invention of Example 5 (deparaffinization condition: 60° C.—10 min., hydration treatment: conducted, matrix solution dispensing pitch: 150 μm). In FIG. 7, (a) represents Bradykinin which is an index, (b) represents a component having m/z=1132.60 of B-Action, (c) represents a component having m/z=976.51 of B-Action, (d) represents a component having m/z=1457.91 of Tublin a3, (e) represents a component having m/z=1053.65, and (f) represents a component having m/z=1515.85, with different colors for different peak intensities of the mass spectrum.

FIG. 10 shows images (a') to (f') obtained by superimposing an actual image (b) after dispensing of matrix in FIG. 8, on the images (a) to (f) of FIG. 9.

While concrete forms within the scope of the present invention have been described in the above Examples, the present invention may be practiced in various other forms without limited to these. Accordingly, the above Examples are given merely for exemplification in every terms, and should not be interpreted in a limitative manner. Further, any modifications within equivalents of claims are included in the scope of the present invention.

The invention claimed is:
1. A method of preparing a sample for matrix-assisted laser desorption/ionization mass spectrometry comprising the steps of:
 preparing a solution of 2,5-dihydroxy benzoic acid of 40 mg/mL to saturated concentration as a matrix solution; and
 dispensing the matrix solution from an inkjet mechanism onto a surface of a sample to be analyzed, to crystallize the 2,5-dihydroxy benzoic acid, wherein the sample to be analyzed is a biological specimen held on a surface of a support by sticking, or the sample to be analyzed is a biological sample transferred from a biological specimen to a surface of a support, and wherein the biological specimen comprises an intact structure from a living body.

2. The method of preparing a sample for matrix-assisted laser desorption/ionization mass spectrometry according to claim 1, wherein the biological specimen is a section specimen.

3. The method of preparing a sample for matrix-assisted laser desorption/ionization mass spectrometry according to claim 1, wherein the biological specimen is derived from a paraffin-embedded specimen.

4. The method of preparing a sample for matrix-assisted laser desorption/ionization mass spectrometry according to claim 1, wherein the support is an electrically conductive support.

5. The method of preparing a sample for matrix-assisted laser desorption/ionization mass spectrometry according to claim 1, wherein the matrix solution is dispensed at a dispensing pitch of 100 to 200 μm.

6. A matrix-assisted laser desorption/ionization mass spectrometry, comprising the steps of:
preparing a sample for matrix-assisted laser desorption/ionization mass spectrometry by the method according to claim 1, and
measuring the sample by a mass spectrometer.

7. The matrix-assisted laser desorption/ionization mass spectrometry according to claim 6, wherein in the step of measuring by a mass spectrometer, second or higher order of multi-stage MS is conducted.

8. A sample for matrix-assisted laser desorption/ionization mass spectrometry prepared by the method according to claim 1.

* * * * *